US006318876B1

(12) United States Patent
Sigro et al.

(10) Patent No.: US 6,318,876 B1
(45) Date of Patent: Nov. 20, 2001

(54) ILLUMINATED ARTIFICIAL PLANT

(76) Inventors: Curt J. Sigro; Sheila Sigro, both of 17160 Lennane, Redford, MI (US) 48240

( * ) Notice: Subject to any disclaimer, the term of this patent is extended or adjusted under 35 U.S.C. 154(b) by 0 days.

(21) Appl. No.: 09/388,584

(22) Filed: Sep. 2, 1999

(51) Int. Cl.[7] ................................................. A47G 33/06
(52) U.S. Cl. ........................ 362/122; 362/96; 362/101; 362/255; 362/806; 362/123; 362/567; 362/568; 422/125; 422/4; 422/305; 422/306
(58) Field of Search .......................... 362/96, 101, 255, 362/806, 122, 123, 567, 568; 422/125, 4, 305, 306

(56) References Cited

U.S. PATENT DOCUMENTS

| 1,938,736 | 12/1933 | Berman | 240/10 |
|---|---|---|---|
| 3,906,215 | 9/1975 | Dinicola | 240/10 R |
| 4,646,209 | 2/1987 | Jansen | 362/122 |
| 4,708,851 | * 11/1987 | Freytag Von Loringhoven | 422/123 |
| 4,789,572 | 12/1988 | Weaver | 428/26 |
| 5,063,485 | * 11/1991 | Harris | 362/122 |
| 5,158,355 | 10/1992 | Sarate | 362/122 |
| 5,455,750 | * 10/1995 | Davis et al. | 362/123 |
| 5,776,559 | * 7/1998 | Woolford | 428/18 |
| 6,067,940 | * 6/2000 | Sanford, Jr. | 362/253 |
| 6,197,263 | * 3/2001 | Blount | 422/125 |

* cited by examiner

Primary Examiner—Stephen Husar
Assistant Examiner—Anabel Ton
(74) Attorney, Agent, or Firm—Joseph N. Breaux

(57) ABSTRACT

An artificial flower arrangement that includes a number of lights and also includes a scent generating mechanism for dispensing a scent into the room. The scent generating mechanism is a plug in air freshener. Each of the light bulbs is positioned in the center of the corolla of an artificial flower.

1 Claim, 3 Drawing Sheets

ILLUMINATED ARTIFICIAL PLANT

TECHNICAL FIELD

The present invention relates to decorative items and more particularly to an illuminated artificial plant that includes a pot assembly, a number of artificial flower structures attached to the pot assembly, and an electric air freshener assembly in connection with the pot assembly; the pot assembly including a pot portion having an electrical supply cord, a power outlet provided on the pot assembly and in electrical connection with the electrical supply cord and a power control switch including an off position, an on position and a blink position; the artificial flower structures each having a bulb socket positioned at the center of the corolla thereof that is in electrical connection with the electrical supply cord through the power control switch; the electric air freshener assembly including a slip in air freshener cartridge and an electrically powered cartridge warming device that is plugable into the power outlet provided on an exterior of the pot portion of the pot assembly; each of the bulb sockets having a light bulb in electrical connection therewith such that operation of all of the light bulbs is controlled by the state of the power control switch.

BACKGROUND ART

Artificial flower arrangements are often used as decorations. It would be desirable, therefore, to have an artificial flower arrangement that included a number of lights and also included a scent generating mechanism for dispensing a scent into the room.

GENERAL SUMMARY DISCUSSION OF INVENTION

It is thus an object of the invention to provide an illuminated artificial plant that includes a pot assembly, a number of artificial flower structures attached to the pot assembly, and an electric air freshener assembly in connection with the pot assembly; the pot assembly including a pot portion having an electrical supply cord, a power outlet provided on the pot assembly and in electrical connection with the electrical supply cord and a power control switch including an off position, an on position and a blink position; the artificial flower structures each having a bulb socket positioned at the center of the corolla thereof that is in electrical connection with the electrical supply cord through the power control switch; the electric air freshener assembly including a slip in air freshener cartridge and an electrically powered cartridge warming device that is plugable into the power outlet provided on an exterior of the pot portion of the pot assembly; each of the bulb sockets having a light bulb in electrical connection therewith such that operation of all of the light bulbs is controlled by the state of the power control switch.

Accordingly, an illuminated artificial plant is provided. The illuminated artificial plant includes a pot assembly, a number of artificial flower structures attached to the pot assembly, and an electric air freshener assembly in connection with the pot assembly; the pot assembly including a pot portion having an electrical supply cord, a power outlet provided on the pot assembly and in electrical connection with the electrical supply cord and a power control switch including an off position, an on position and a blink position; the artificial flower structures each having a bulb socket positioned at the center of the corolla thereof that is in electrical connection with the electrical supply cord through the power control switch; the electric air freshener assembly including a slip in air freshener cartridge and an electrically powered cartridge warming device that is plugable into the power outlet provided on an exterior of the pot portion of the pot assembly; each of the bulb sockets having a light bulb in electrical connection therewith such that operation of all of the light bulbs is controlled by the state of the power control switch.

BRIEF DESCRIPTION OF DRAWINGS

For a further understanding of the nature and objects of the present invention, reference should be made to the following detailed description, taken in conjunction with the accompanying drawings, in which like elements are given the same or analogous reference numbers and wherein.

EXEMPLARY MODE FOR CARRYING OUT THE INVENTION

Figure 1:
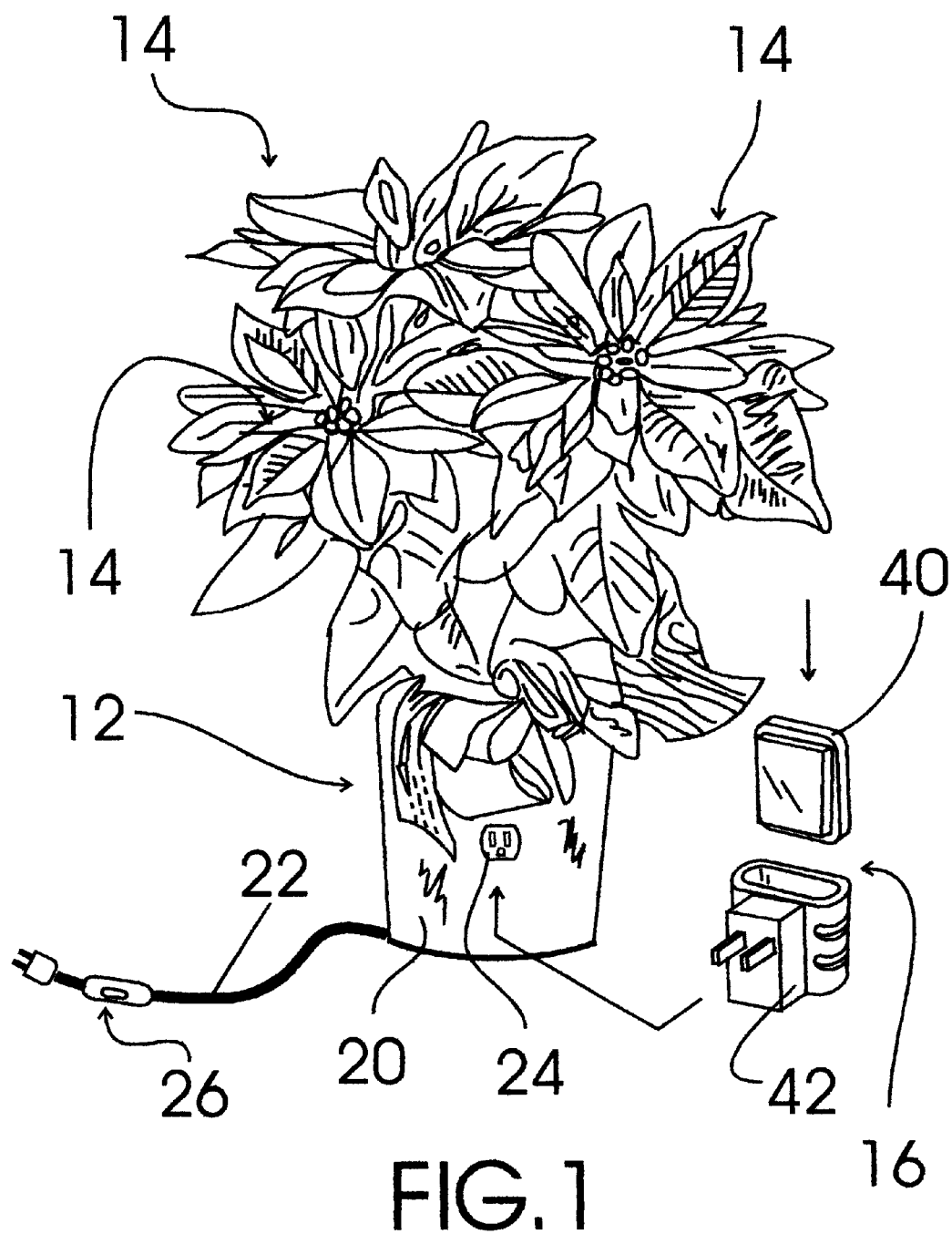
FIG. 1 is a perspective view of an exemplary embodiment of the illuminated artificial plant of the present invention showing the pot assembly including a pot portion having an electrical supply cord, a power outlet provided on the pot assembly and in electrical connection with the electrical supply cord and a power control switch including an off position, an on position and a blink position; the artificial flower structures attached to the pot assembly and each having a bulb socket positioned at the center of the corolla thereof that is in electrical connection with the electrical supply cord through the power control switch; and the electric air freshener assembly including a slip in air freshener cartridge and an electrically powered cartridge warming device that is plugable into the power outlet provided on an exterior of the pot portion of the pot assembly; each of the bulb sockets having a light bulb in electrical connection therewith such that operation of all of the light bulbs is controlled by the state of the power control switch.

FIG. 1 shows an exemplary embodiment of the illuminated artificial plant of the present invention, generally designated 10. Illuminated artificial plant 10 includes a pot assembly, generally designated 12; a number of artificial flower structures, each generally designated 14, attached to pot assembly 12; and an electric air freshener assembly, generally designated 16, in connection with pot assembly 12. Pot assembly 12 including a pot portion 20 having an electrical supply cord 22, a power outlet 24 provided on the exterior thereof that is in electrical connection with electrical supply cord 22, and a power control switch 26.

Figure 2:
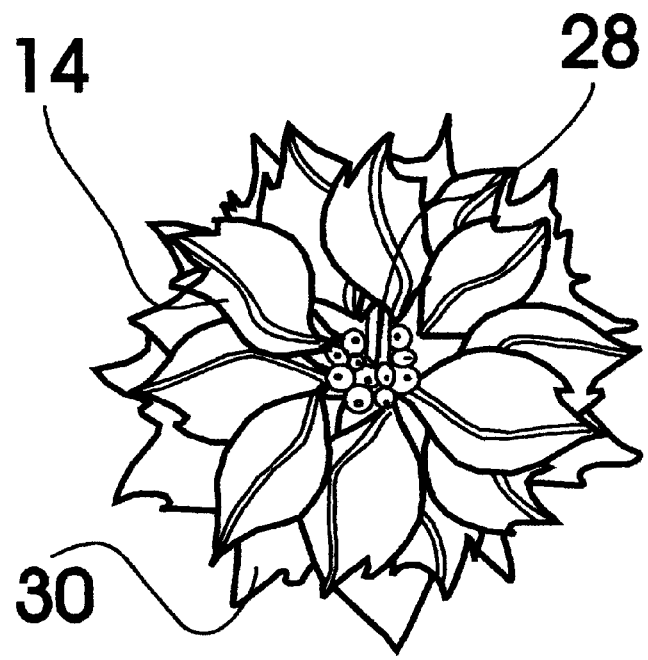
FIG. 2 is a top plan view of one of the artificial flower structures showing a light bulb positioned at the center of the corolla thereof.
Figure 3:
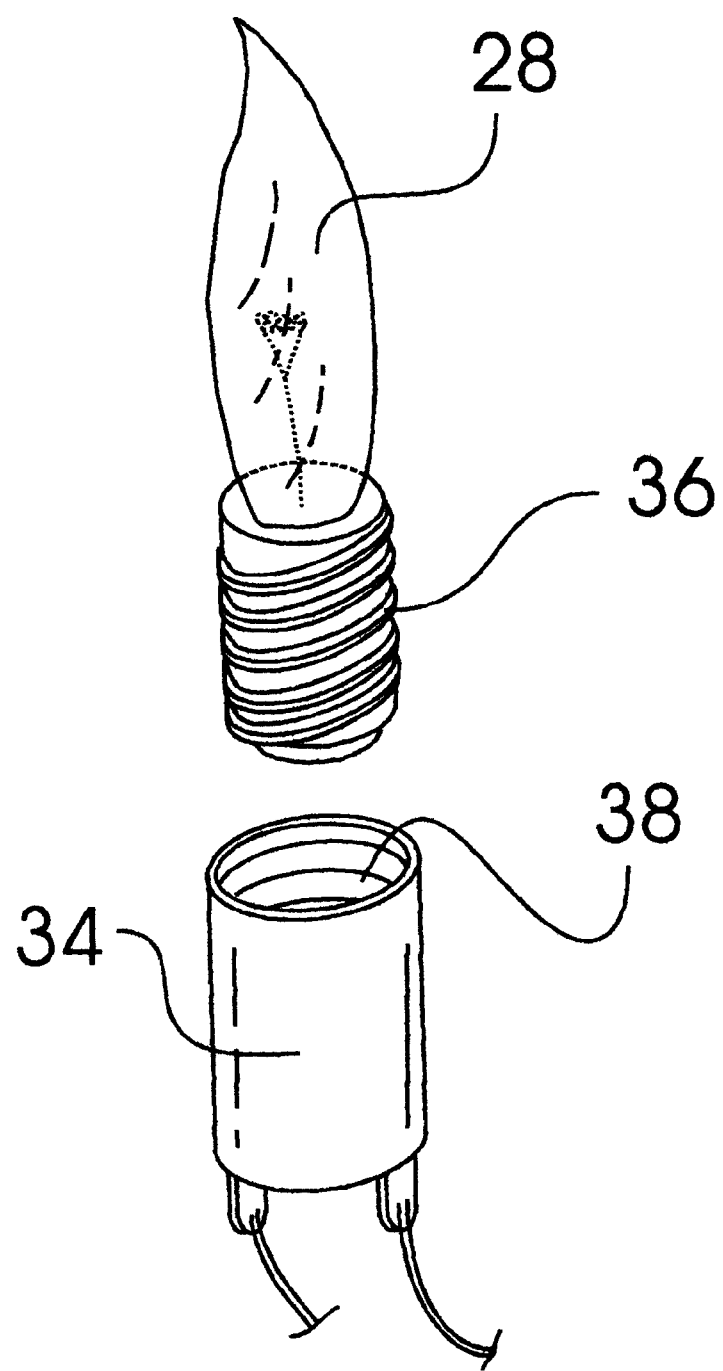
FIG. 3 is an exploded plan view showing the light bulb positioned above the bulb socket.

Referring to FIG. 2, each artificial flower structure 14 includes a light bulb 28 positioned at the center of a corolla 30 thereof that is in electrical connection with electrical supply cord 22 through power control switch 26 and, referring to FIG. 3, a bulb socket 34. Threads 36 on light bulb 28 are screwed into an internally threaded cavity 38 of bulb socket 34.

Referring back to FIG. 1, electric air freshener assembly 16 includes a slip in air freshener cartridge 40 and an electrically powered cartridge warming device 42 that is plugable into power outlet 24.

Figure 4:
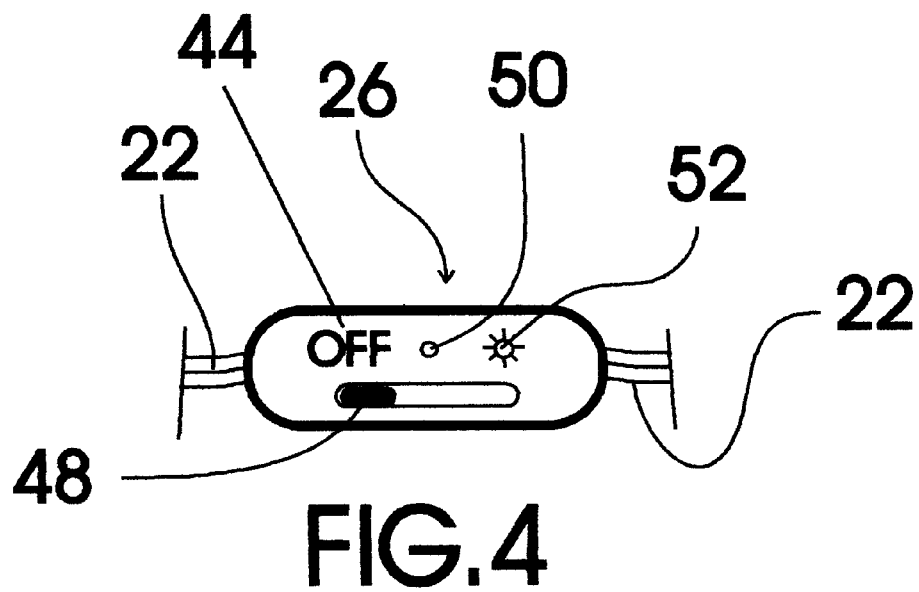
FIG. 4 is a top plan view of the power control switch showing the slide positionable state selector switch and the off, the on and the blink selector indicators.

Referring to FIG. 4, power control switch 26 includes a slide positionable state selector switch 48 that is slidable into an "off" position 44, an "on" position 50, and a "blink" position 52. Operation of all of the light bulbs 28 (FIGS. 2 and 3) is controlled by power control switch 26.

It can be seen from the preceding description that an illuminated artificial plant has been provided that includes a pot assembly, a number of artificial flower structures attached to the pot assembly, and an electric air freshener assembly in connection with the pot assembly; the pot assembly including a pot portion having an electrical supply cord, a power outlet provided on the pot assembly and in electrical connection with the electrical supply cord and a power control switch including an off position, an on position and a blink position; the artificial flower structures each having a bulb socket positioned at the center of the corolla thereof that is in electrical connection with the electrical supply cord through the power control switch; the electric air freshener assembly including a slip in air freshener cartridge and an electrically powered cartridge warming device that is plugable into the power outlet provided on an exterior of the pot portion of the pot assembly; each of the bulb sockets having a light bulb in electrical connection therewith such that operation of all of the light bulbs is controlled by the state of the power control switch.

It is noted that the embodiment of the illuminated artificial plant described herein in detail for exemplary purposes is of course subject to many different variations in structure, design, application and methodology. Because many varying and different embodiments may be made within the scope of the inventive concept(s) herein taught, and because many modifications may be made in the embodiment herein detailed in accordance with the descriptive requirements of the law, it is to be understood that the details herein are to be interpreted as illustrative and not in a limiting sense.

What is claimed is:

1. An illuminated artificial plant comprising:

a pot assembly;

a number of artificial flower structures attached to said pot assembly; and an electric air freshener assembly in connection with said pot assembly;

said pot assembly including a pot portion having an electrical supply cord, a power outlet provided on said pot assembly and in electrical connection with said electrical supply cord and a power control switch including an off position, an on position and a blink position;

said artificial flower structures each having a bulb socket positioned at said center of said corolla thereof that is in electrical connection with said electrical supply cord through said power control switch;

said electric air freshener assembly including a slip in air freshener cartridge and an electrically powered cartridge warming device that is plugable into said power outlet provided on an exterior of said pot portion of said pot assembly;

each of said bulb sockets having a light bulb in electrical connection therewith such that operation of all of said light bulbs is controlled by said state of said power control switch.

* * * * *